United States Patent [19]
Wijay

[11] Patent Number: 5,707,387
[45] Date of Patent: Jan. 13, 1998

[54] FLEXIBLE STENT

[76] Inventor: Bandula Wijay, 1903 Carriage Creek Dr., Friendswood, Tex. 77546

[21] Appl. No.: 621,481
[22] Filed: Mar. 25, 1996
[51] Int. Cl.$^6$ .......................... A61M 5/00; A61M 29/00; A61F 2/02
[52] U.S. Cl. ................. 606/194; 623/1; 606/198
[58] Field of Search ..................... 606/195, 198, 606/192, 194, 197; 623/1, 12; 128/898

[56] References Cited

U.S. PATENT DOCUMENTS

| | | |
|---|---|---|
| Re. 34,037 | 8/1992 | Innue et al. . |
| 4,503,559 | 3/1985 | Dotter . |
| 4,580,568 | 4/1986 | Gianturco . |
| 4,732,152 | 3/1988 | Wallsten et al. . |
| 4,739,762 | 4/1988 | Palmaz ........................... 604/104 X |
| 4,740,207 | 4/1988 | Kreamer . |
| 4,776,337 | 10/1988 | Falmaz . |
| 4,795,458 | 1/1989 | Regan . |
| 4,820,298 | 4/1989 | Lavaen et al. . |
| 4,886,062 | 12/1989 | Wiktor . |
| 4,913,141 | 4/1990 | Hillstead . |
| 4,950,227 | 8/1990 | Savin et al. . |
| 4,964,853 | 10/1990 | Sugiyama et al. . |
| 4,969,458 | 11/1990 | Wiktor . |
| 4,990,151 | 2/1991 | Wallston . |
| 5,100,429 | 3/1992 | Sinofsky et al. . |
| 5,108,416 | 4/1992 | Ryan et al. . |
| 5,133,732 | 7/1992 | Wiktor . |
| 5,135,536 | 8/1992 | Hillstead . |
| 5,139,480 | 8/1992 | Hickle et al. . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froix . |
| 5,163,958 | 11/1992 | Pinchuk . |
| 5,195,984 | 3/1993 | Schatz . |
| 5,197,978 | 3/1993 | Hess . |
| 5,213,561 | 5/1993 | Weinstein et al. . |
| 5,222,969 | 6/1993 | Gillis . |
| 5,222,971 | 6/1993 | Willard et al. . |
| 5,234,457 | 8/1993 | Anderson . |
| 5,258,042 | 11/1993 | Mahta . |
| 5,266,073 | 11/1993 | Wall . |
| 5,282,823 | 2/1994 | Schwartz et al. . |
| 5,282,824 | 2/1994 | Gianturco . |
| 5,287,861 | 2/1994 | Wilk . |
| 5,292,331 | 3/1994 | Boneau . |
| 5,304,121 | 4/1994 | Sahatjian . |
| 5,306,294 | 4/1994 | Winston et al. . |
| 5,314,472 | 5/1994 | Fontaine . |
| 5,334,201 | 8/1994 | Cowan . |
| 5,336,518 | 8/1994 | Narayanan et al. . |
| 5,342,348 | 8/1994 | Kaplan . |
| 5,344,426 | 9/1994 | Lau et al. . |

(List continued on next page.)

FOREIGN PATENT DOCUMENTS

| | | |
|---|---|---|
| 421 729 A2 | 4/1991 | European Pat. Off. . |
| 621 017 A1 | 4/1994 | European Pat. Off. . |
| 662 307 A1 | 7/1995 | European Pat. Off. . |

OTHER PUBLICATIONS

Angiostent Balloon Expandagle Stent System, AngioDynamics Division of E-Z-EM, Inc., Sep., 1994.
Gianturco-Roubin Flex-Stent Coronary Stents, Cook Cardiology, 1995 (brochure).

Primary Examiner—Michael Buiz
Assistant Examiner—Nancy Connolly Mulcare
Attorney, Agent, or Firm—Rosenblatt & Redano P.C.

[57] ABSTRACT

A tubular stent is disclosed that is made of a series of bands having a generally tubular shape with an open end. Each band has an open rectangular form made of an elongated material. The bands have the open ends (or interruptions) in an offset manner and each band has crosstie or ties which are either rigid or flexible. Ties, even if they are straight, can be disposed close to each other, or further away from each other, and can vary in number in order to adjust the relative stiffness of the stent. Each of the bands are preferably a generally rectangular shape and can be made from a wire of a variety of different cross-sections, or can be cut from a flat sheet, or burned out of a cylindrical shape.

14 Claims, 3 Drawing Sheets

U.S. PATENT DOCUMENTS

| | | |
|---|---|---|
| 5,354,309 | 10/1994 | Schnepp-Peschetal ............ 606/198 |
| 5,360,401 | 11/1994 | Turnland . |
| 5,368,566 | 11/1994 | Crocker . |
| 5,370,691 | 12/1994 | Samson . |
| 5,383,928 | 1/1995 | Scott et al. . |
| 5,389,106 | 2/1995 | Tower . |
| 5,391,172 | 2/1995 | Williams et al. . |
| 5,397,355 | 3/1995 | Marin et al. . |
| 5,403,341 | 4/1995 | Solar . |
| 5,421,955 | 6/1995 | Lau et al. . |
| 5,423,885 | 6/1995 | Williams . |
| 5,433,706 | 7/1995 | Abiuso . |
| 5,437,632 | 8/1995 | Engleson . |
| 5,439,444 | 8/1995 | Anderson et al. . |
| 5,439,445 | 8/1995 | Kontos . |
| 5,443,500 | 8/1995 | Sigwart . |
| 5,449,373 | 9/1995 | Pinchasik et al. ............ 623/1 |
| 5,480,423 | 1/1996 | Ravenscroft et al. . |
| 5,545,210 | 8/1996 | Hess et al. ............ 606/198 X |
| 5,549,662 | 8/1996 | Fordenbacher ............ 623/1 |
| 5,556,413 | 9/1996 | Lam ............ 606/198 |
| 5,591,223 | 1/1997 | Lock et al. ............ 623/1 |
| 5,603,722 | 2/1997 | Phan et al. ............ 606/198 |

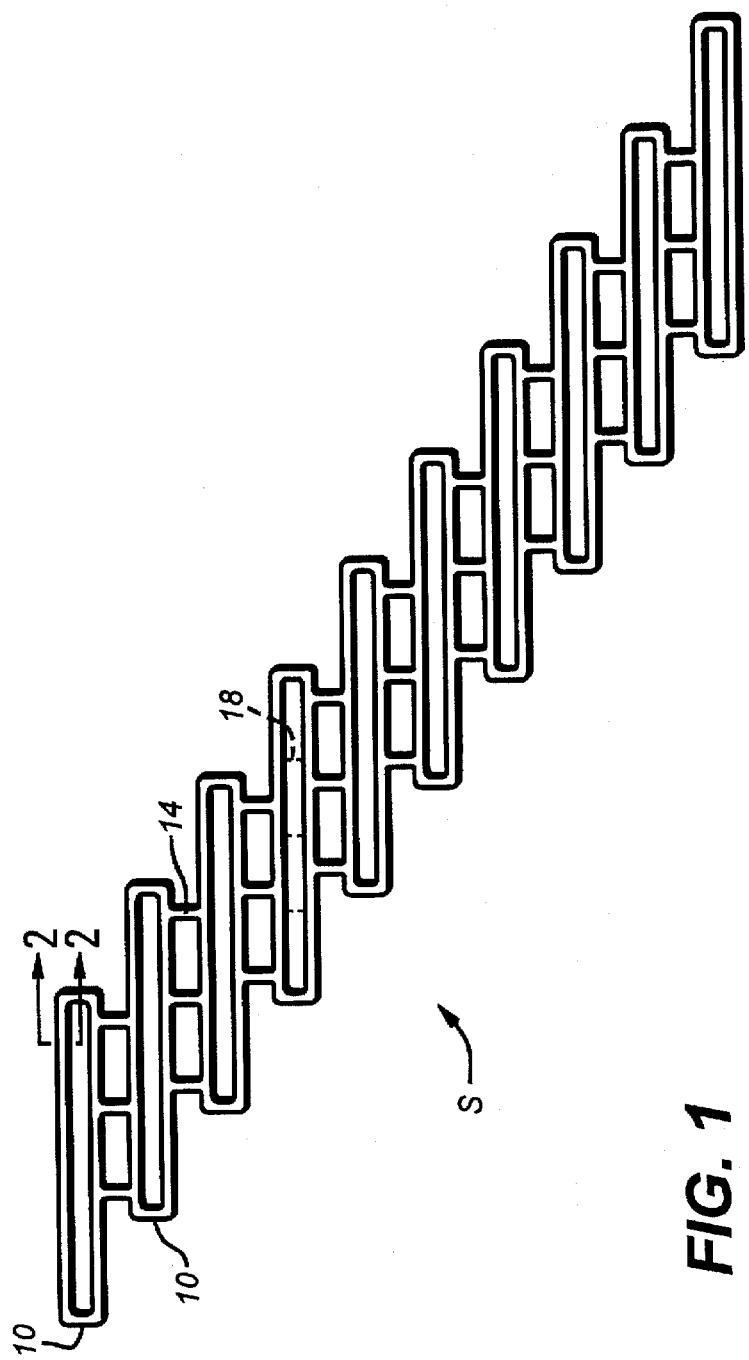
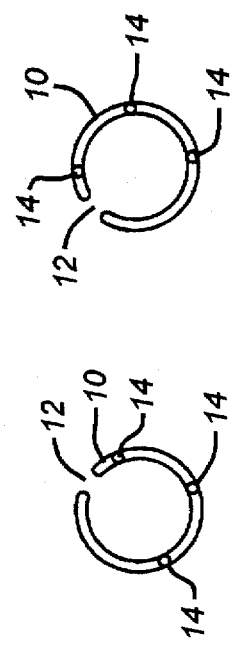
FIG. 1
FIG. 2
FIG. 3
FIG. 4

FLEXIBLE STENT

FIELD OF THE INVENTION

The field of this invention relates to vascular stents that can be delivered to a predetermined position and allowed to spring outwardly or, in the alternative, which can be expanded in place.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stents are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, U.S. Pat. Nos. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthus Fontaine, U.S. Pat. No. 5,370,683, also describes a similar device where a flat wire form of sinusoidal shape is wound on a mandrel to form a helical coil. The wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The preshaped wire form (sinusoidal in most of the prior art) is wrapped on a mandrel to form a coil. However, the forces imported by the vessel wall's hoop strength are radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in Scott U.S. Pat. No. 5,383,928 or Gene Samson U.S. Pat. No. 5,370,691 or Rolando Gills U.S. Pat. No. 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. Nos. 4,733,665; 4,739,762; 4,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

U.S. Pat. No. 5,443,500 illustrates the use of square openings with rectangular prongs that stick therethrough to lock the stent. This design, as well as other locking mechanisms, generally have resulted in very stiff stents because of the use of a tubular-type grid construction. Further, the locking devices have resulted in sharp outwardly oriented tabs which are used for the locking, which could cause vascular damage.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent, while the plain ends on such an arrangement which are snipped off offer the potential of sharp points which can puncture or damage the intima. On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 04217292.

Often these stents are layered with polymeric sheaths that are impregnated with biocompatible substances or can be coated with heparin or hydrogel. Most sheath-type coatings reduce endothelial cell growth through the stent, which is a major requirement in successful stenting of body cavities such as arteries and veins.

Several parameters in design of stents are important. Of the more important parameters is the issue of recoil. Recoil deals with the memory of the stent material which, generally speaking, upon expansion in the blood vessel will want to recoil back to its original shape. This can be problematic because it is desirable for the stent, once expanded, to remain in good contact with the vessel wall to avoid longitudinal shifting. Furthermore, any recoil constricts the flow passage and presents a greater portion of the stent in the blood flowpath, thus creating additional complications due to the turbulence which ensues.

Related to the concern regarding recoil is another concern regarding component twist. This phenomenon generally occurs when the cross-sectional area of the components is rectangular, such as when the stent is manufactured from a cylindrical piece which is then cut by lasers or other means to form the particular pattern. Particularly in the honeycombed designs involving the use of square or rectangular element cross-sections, radial expansion of such stents generally results in a twist of the component segments such that they extend into the flowpath in the artery or vein. Again, this causes turbulence which is undesirable.

Related to the problem of recoil or constriction after expansion is the ability of the stent to anchor itself in the vascular wall. An anchoring system that does not cause trauma is a desirable feature not found in the prior art.

Yet other considerations which are desirable in a stent not found in the prior art is the flexibility to be maneuvered around bends in the vascular system, coupled with the ability to conform to a bend without kinking or leaving large open areas. The stents of the present invention have the objective of addressing the issue of recoil, as well as providing an anchoring mechanism to fixate the stent once set. Several of the designs incorporate flexibility to allow the stent to follow a bend or curve in a vascular flowpath while a the same time providing sufficient radial deformation to ensure proper fixation while minimizing angular twisting movements of the stent components to minimize turbulence through the stent.

In a recent article appearing in late 1995, by Dr. Donald S. Baim, entitled "New Stent Designs," a description is given of the ideal endovascular prosthesis. There, Dr. Baim indicates that the ideal stent should have low implantation profile with enhanced flexibility to facilitate delivery. He goes on to say that the stent should be constructed from a noncorrosive, nonthrombogenic radiopaque alloy and have expanded geometry which maximizes radial strength to resist vascular recoil. The ideal stent described by Baim is further described as having a wide range of diameters and lengths. Dr. Baim concludes that it is unlikely that any current designs satisfy all these requirements. Thus, one of the objectives of the present invention is to go further than the prior designs in satisfying the criteria for the ideal designs as set forth by Dr. Baim in his recent article.

SUMMARY OF THE INVENTION

A tubular stent is disclosed that is made of a series of bands having a generally tubular shape with an open end. Each band has an open rectangular form made of an elongated material. The bands have the open ends (or interruptions) in an offset manner and each band has crosstie or ties which are either rigid or flexible. Ties, even if they are straight, can be disposed close to each other, or further away from each other, and can vary in number in order to adjust the relative stiffness of the stent. Each of the bands are preferably a generally rectangular shape and can be made from a wire of a variety of different cross-sections, or can be cut from a flat sheet, or burned out of a cylindrical shape.

BRIEF DESCRIPTION OF THE DRAWINGS

FIG. 1 is a flattened view of the stent prior to rolling into a tubular shape showing straight crossties between a plurality of bands.

FIG. 2 is a section along lines 2—2 of FIG. 1 showing some alternative cross-sectional shapes for the bands which comprise the tubular structure of the stent.

FIG. 3 is a top view of the unrolled stent of FIG. 1 showing the break in the top band.

FIG. 4 is similar to FIG. 3 in that it shows the next band adjacent to the band illustrated in FIG. 3 showing how the openings in each band are offset.

DETAILED DESCRIPTION OF THE PREFERRED EMBODIMENT

Figure 6:
FIG. 6 is a section along line 6—6 of FIG. 5 showing the variety of some of the cross-sections that can be employed for the stent.

The stent of the present invention is shown in an unrolled condition in FIG. 1. In order to make the stent S shown in FIG. 1, the pattern indicated in FIG. 1 can be cut from a flat sheet and rolled around a mandrel (not shown). The stent comprises a series of bands 10. Each band in FIG. 1 is a generally rectangular form and preferably any closed form. Any loose ends could form sharp points which could damage the vascular wall and, therefore, should preferably be avoided. When each of the bands 10 is rolled around a mandrel of a suitable diameter, the mandrel size is selected such that upon rolling around the mandrel, each of the bands 10 has an interruption or gap 12, as shown in FIGS. 3 and 4. The width of the gap can vary depending on the stiffness desired. The interruption or gap is preferably aligned with the longitudinal axis of the stent S. For example, FIG. 3 could relate to the top band shown in FIG. 1 with FIG. 4 of the band 10 immediately underneath. As can be seen by the layout in which the stent S is cut from FIG. 1, the gaps 12 will be offset from one band 10 to the next adjacent band. The angular offset of gaps 12 between bands 10 can be varied to achieve varying degrees of stiffness. Each of the bands 10 are joined together by one or more crossties 14. In the embodiment of FIG. 1, the crossties are straight and there are three between each of the bands 10. The crossties 14 tend to be gathered at one side of each band 10 and on one side of gap 12 as opposed to distributed over its length, as shown by the designs in FIGS. 5 and 7. FIG. 3 also shows the manner in which the crossties 14 are disposed with respect to the gap 12. Because the gap 12 in each band is offset from the gap 12 in the band 10 adjacent to it, the crossties between respective bands 10 are also offset from each other, as illustrated by comparing FIGS. 3 and 4. FIG. 2 illustrates that the cross-section can be round, rectangular, oval, elliptical, or some other shape. The stent of FIG. 1 can be made from using laser etching from a cylindrical shape, or using a cutting from a flat shape, or using a wire of the desired cross-section and forming the shapes of the bands 10.

Figure 5:
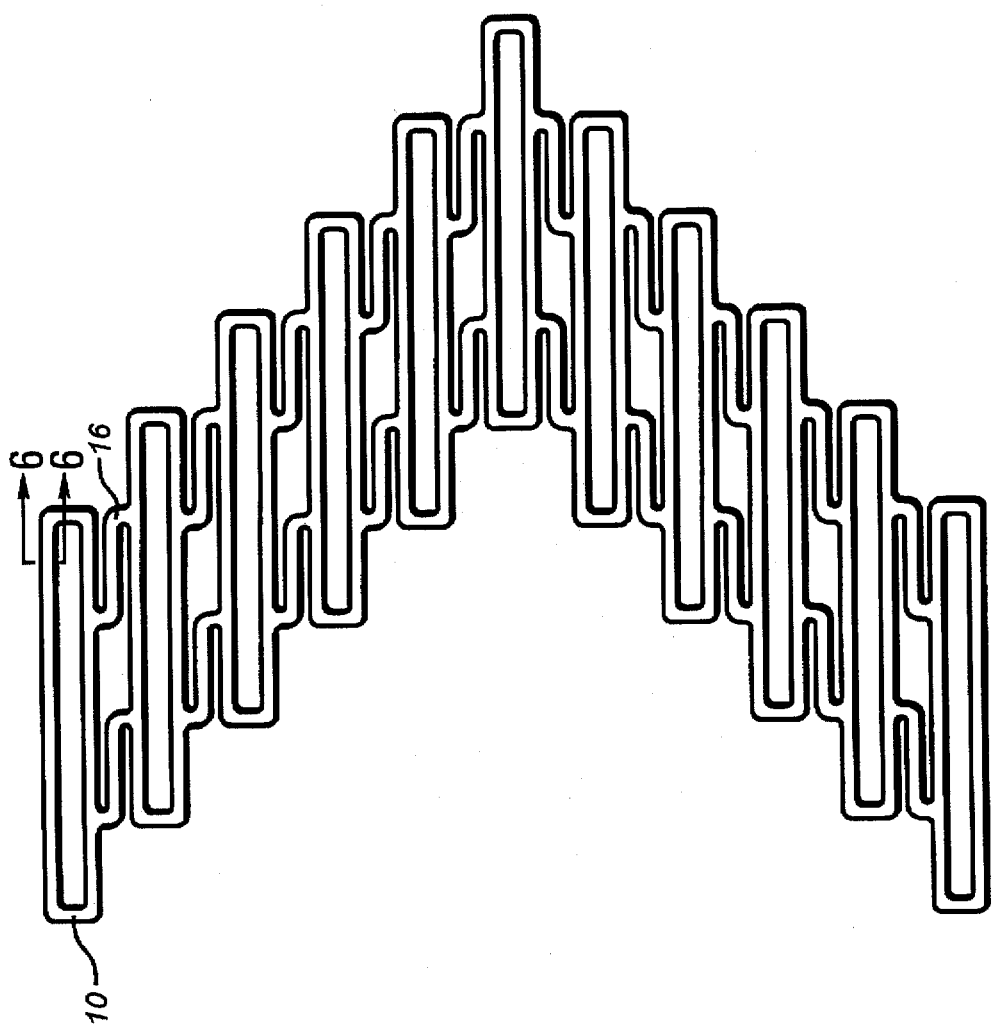
FIG. 5 is an alternative embodiment of the stent of FIG. 1 showing flexible crossties.
Figure 9:
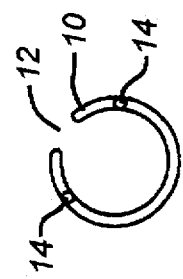
FIG. 9 is a top view of the stent of FIG. 7.
Figure 8:
FIG. 8 is a section along line 8—8 of FIG. 7.
Figure 7:
FIG. 7 is another embodiment to the stent of FIGS. 1 and 5 showing the crossties further spaced apart and generally closer to the open segment of each band.

FIG. 5 illustrates that instead of using the straight crossties 14, as illustrated in FIG. 1, generally S-shaped crossties 16 can be used which are far more flexible. The construction of the stent made from the flat pattern illustrated in FIG. 5 is in other ways similar to the design of FIG. 1 in that there are a plurality of bands 10, each with a gap, such as 12, illustrated in FIGS. 3 and 4. Once again, FIG. 6 illustrates the variety of cross-sections that can be used with the stent of design No. 5, while FIG. 8 illustrates the same designs of cross-sectional area that can be used with the stent shown in FIG. 7. Comparing the stent of FIGS. 1 and 7, it can be seen that the crossties 14 are now much further apart and fewer in number. FIG. 7 illustrates the use of two straight crossties very close to the gap 12, which is ultimately formed by each of the bands 10 in a design of FIG. 7. The design of FIG. 7 will necessarily be stiffer than the design of FIG. 1 since the crossties 14 are disposed closer to each opening 12 in each of the bands 10 that form the stent of FIG. 7. The crossties can also be mixed and matched so that they are all straight, some straight and some with one or more bends, or all with one or more bends.

Additional changes can be made to affect the relative stiffness of the stent. For example, as shown in FIG. 1, in dashed lines 18, each of the bands 10 can be further reinforced to make them stiffer by putting one or more ribs 18 within each band. The overall configuration of the band 10 can be revised without departing from the spirit of the invention to include one or more geometric generally open shapes. The overall periphery of each band 10 can still have the generally rectangular shape, however, it can be formed of a series of square shapes, or other shapes, and still fall within the purview of the invention.

It can be appreciated that the flexible S-shape bands 16 of FIG. 5 can lend considerable flexibility to the stent when it is formed into that tubular shape necessary for insertion into the vascular system. In fact, the stent can be made sufficiently flexible to be bent so that one end touches the opposite end twisting the stent into a generally U-shape and still have it spring back and retain its original shape without any kinking. The designs illustrated in FIGS. 1, 5, and 7 also add other advantages in that when there is any bending to conform to the vascular structure, no wide gaps open in the section of the stent that is under tension, while at the same time the opposite end of the stent that is in compression due to a bend doesn't completely collapse and generally retains its original shape upon its insertion with minor deflection to accommodate the vascular structure. At the same time the use of geometric forms which are closed, such as a rectangular shape, provides sufficient strength to resist recoil after expansion. The gaps 12 allow radial expansion to anchor the stent S. The gaps 12 also allow minor diameter changes to the stent S. Offsetting the gaps lends uniformity to the stent and avoids giving it undue stiffness along a longitudinal line akin to a "spine."

The flexibility of the stents shown in FIGS. 1, 5, and 7 is also a function of the opening 12 in each of the bands and the offset nature of these openings. Further combining with these features is the use of a band structure made of an elongated material formed into the preferable rectangular shape. The materials that stents can be made of are well known to those skilled in the art. Some preferred materials are stainless steel, nickel titanium alloys or tantalum. The stents can be built to be self-expanding such as for example if a nickel-titanium alloy is used. Alternatively, the stent can be delivered and expanded in place by using a balloon catheter or any other delivery/expansion device such as disclosed in co-pending U.S. application Ser. No. 08/603, 267, filed Feb. 20, 1996, which is incorporated as if fully set forth. Using such materials and known techniques of cutting or drawing, bands 10 can be manufactured from sheet, from tube, or by other processes from elongated wire-like materials having any of the cross-sections shown in FIG. 2 or other suitable cross-sections which are functionally equivalent and operationally similar.

The foregoing disclosure and description of the invention are illustrative and explanatory thereof, and various changes in the size, shape and materials, as well as in the details of the illustrated construction, may be made without departing from the spirit of the invention.

I claim:

1. A stent comprising

A plurality of bands, each said band composed of an elongated solid wire-like material formed into a closed and substantially rectangular shape, said substantially rectangular shape having two ends, a longitudinal axis along its length and extending between said two ends, and a horizontal axis;

wherein each band is offset from the adjacent band such that the corresponding band ends are offset from each other; and wherein at least one cross-tie member extends between each pair of adjacent bands thereby connecting said bands; and wherein said plurality of bands are adapted to be rolled about said band horizontal axis to form a cylindrical stent having a gap between the two ends of each rolled band thus resulting in adjacent bands having relatively offset gaps; and wherein said bands are adapted to move such that the size of the gap changes in order to accommodate necessary changes in the cylindrical shape of the stent.

2. The stent of claim 1, wherein:

said crossties are disposed adjacent and in close proximity to and on either side of said interruption on each said band.

3. The stent of claim 1, wherein:

said crossties are disposed adjacent each other and closer to one side of the gap then they are to the other side of the gap.

4. The stent of claim 1, further comprising:

each band has an open generally rectangular form.

5. The stent of claim 1, further comprising:

at least some of said crossties are substantially straight.

6. The stent of claim 1, further comprising:

at least some of said crossties contain at least one bend.

7. The stent of claim 6, further comprising:

all of said crossties contain at least two bends.

8. The stent of claim 1, further comprising:

all of said crossties are substantially straight.

9. The stent of claim 2, further comprising:

at least some of said crossties are substantially straight.

10. The stent of claim 2, further comprising:

all of said crossties are substantially straight.

11. The stent of claim 1, further comprising:

said bands are self-expanding for placing the stent.

12. The stent of claim 1, further comprising:

said bands are expandable with a delivery device for placing the stent.

13. The stent of claim 8, further comprising:

said bands are self-expanding for placing the stent.

14. The stent of claim 8, further comprising:

said bands are expandable with a delivery device for placing the stent.

* * * * *